United States Patent [19]

Gruber et al.

[11] 4,202,836
[45] May 13, 1980

[54] ACETOXYALKYL CYANOACETATE INTERMEDIATES IN THE MANUFACTURE OF COPOLYMERIZABLE, ULTRAVIOLET LIGHT ABSORBER COMPOUNDS

[75] Inventors: Bruce A. Gruber, Bloomingdale; Donald H. Lorenz, Basking Ridge, both of N.J.

[73] Assignee: GAF Corporation, New York, N.Y.

[21] Appl. No.: 30,753

[22] Filed: Apr. 17, 1979

Related U.S. Application Data

[63] Continuation-in-part of Ser. No. 6,787, Jan. 26, 1979, and a continuation-in-part of Ser. No. 16,134, Mar. 1, 1979, and a continuation-in-part of Ser. No. 22,320, Mar. 19, 1979.

[51] Int. Cl.² .................. C07C 121/00; C07C 121/20
[52] U.S. Cl. .............................. 260/465.4; 260/465 D
[58] Field of Search ...................................... 260/465.4

[56] References Cited

U.S. PATENT DOCUMENTS

| | | | |
|---|---|---|---|
| 2,820,813 | 1/1958 | Smith | 260/465.4 |
| 3,142,698 | 7/1964 | Halpern et al. | 260/465.4 |
| 3,658,878 | 4/1972 | Smith | 260/465.4 |
| 4,041,062 | 8/1977 | Buck | 260/465.4 |

*Primary Examiner*—Joseph Paul Brust
*Attorney, Agent, or Firm*—Walter C. Kehm; Walter Katz

[57] ABSTRACT

This invention relates to acetoxyalkyl cyanoacetate intermediates in the manufacture of copolymerizable, ultraviolet light absorber compounds, said intermediates having the formula:

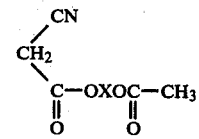

where X is alkylene, $C_2$-$C_{17}$, unsubstituted or substituted with halo, cyano, alkyl, $C_1$-$C_6$, alkoxy, $C_1$-$C_6$ alkoxyalkyl, $C_1$-$C_6$ or alkoxyalkyleneoxy, $C_1$-$C_6$.

The intermediates of this invention are used to make (2-cyano-3,3-diphenylacryloxy) alkylene acrylic acid esters and (2-cyano-3,3-diphenylacryloxy) alkylene ethylenic ethers in high yield.

5 Claims, No Drawings

ACETOXYALKYL CYANOACETATE INTERMEDIATES IN THE MANUFACTURE OF COPOLYMERIZABLE, ULTRAVIOLET LIGHT ABSORBER COMPOUNDS

This application is a continuation-in-part of each of Ser. No. 006,787, filed Jan. 26, 1979, of Ser. No. 016,134, filed Mar. 1, 1979 and of Ser. No. 022,320, filed Mar. 19, 1979.

BACKGROUND OF THE INVENTION

1. Field of the Invention

This invention relates to ultraviolet light absorber compounds, and, more particularly, to intermediates useful in the preparation of such compounds as 2-cyano-3,3-diphenylacryloxy alkylene acrylic acid ester compounds in high yield, which can be copolymerized with vinyl monomers to produce polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material.

Also, it is not possible to use all of these ultraviolet absorbers with radiation curing of the plastic material. Another disadvantage of these ultraviolet absorbers is the high amount of absorber needed for protection of some materials.

RELATED PATENT APPLICATIONS (a) FDN-1157, Ser. No. 006,787, filed Jan. 26, 1979 by the same applicants, and assigned to the same assignee as herein. This application describes novel copolymerizable ultraviolet light absorber compounds which are substantially free of the disadvantages of the prior art, which are (2-cyano-3,3-diphenylacryloxy) alkylene acrylic acid esters.

(b) FDN-1157/A, Ser. No. 016,134, filed Mar. 1, 1979, by the same applicants, and assigned to the same assignee, as herein. This application describes a method of making the compounds referred to in related application FDN-1157 above.

(c) FDN-1157/B, Ser. No. 022,320 filed Mar. 19, 1979, by the same applicants, and assigned to the same assignee, as herein. This application describes novel copolymerizable ultraviolet light absorber compounds, which are (2-cyano-3,3-diphenylacryloxy) alkylene ethylenic ethers.

This application is a continuation in part of the above related patent applications.

SUMMARY OF THE INVENTION

This invention describes novel acetoxyalkyl cyanoacetate intermediates in the manufacture of copolymerizable, ultraviolet light absorber compounds, said intermediates having the formula:

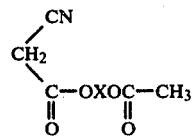

where X is alkylene, $C_2$–$C_{17}$, unsubstituted or substituted with halo, cyano, alkyl, $C_1$–$C_6$ alkoxy, $C_1$–$C_6$ alkoxyalkyl, $C_1$–$C_6$ or alkoxyalkyleneoxy, $C_1$–$C_6$.

The intermediates of this invention are used to make (2-cyano-3,3-diphenylacryloxy) alkylene acrylic acid esters and (2-cyano-3,3-diphenylacryloxy) alkylene ethers in high yield.

DETAILED DESCRIPTION OF THE INVENTION

The intermediate compounds of the invention are made by acrylating a hydroxyalkylene cyanoacetate starting material (I) to form the corresponding acetoxy derivative (II). Acylation usually is carried out by reaction with acetic anhydride or acetyl chloride.

The X groups in the formula above are unsubstituted or substituted alkylene radicals, $C_2$–$C_{17}$. The preferred groups are unsubstituted lower alkylene, $C_2$–$C_6$, which are derived synthetically from ethylene glycol, propylene glycol, butanediol, and the like. The best mode is represented by —$CH_2$—$CH_2$—.

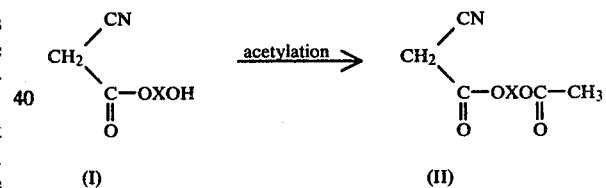

(I)                                          (II)

The intermediate compounds of this invention are condensed with a benzophenone in a Knoevenagel reaction to form the corresponding acetoxyalkyl (2-cyano-3,3-diphenyl) acrylate in excellent yield. The final steps in the synthesis of the desired product comprises hydrolysis of the acetoxy group to convert it to hydroxy, and esterification of the hydroxy compound with acryloyl halide or an acrylic acid.

The method of the invention is particularly advantageous in that it affords both the intermediate and product compounds in high yield. A feature of the process is that protection of the hydroxy group before carrying out the Knoevenagel reaction enables the Knoevenagel condensation to proceed in excellent yield to the desired diphenyl intermediate, whereas previous condensations without protection of the hydroxy group gave very low yields indeed. The protecting acetoxy groups is removed conveniently by hydrolysis under conditions which do not affect the remaining ester portion of the molecule. The final esterification reaction with the acryloyl halide or acrylic acid also is a high yield reaction, and thus the overall sequence of steps gives the desired acrylic acid ester compounds in yields which exceed 30%.

The final compounds are copolymerized, for example, with a urethane oligomer, by radiation curing, to provide useful polymeric coatings.

The following examples will describe the invention with more particularity.

EXAMPLE 1

Acetoxyethyl Cyanoacetate

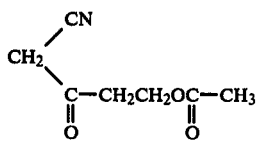

Cyanoacetic acid was esterified with ethylene glycol according to U.S. Pat. No. 3,644,466 (Col. 7–8, Ex. 3) to give the hydroxyethyl cyanoacetate starting material in 74% yield.

Into a 1 l. three-neck round bottom flask with magnetic stirrer, dropping funnel, thermometer, and drying tube was charged 122 g. (1.2 moles) of acetic anhydride and 10 drops of concentrated sulfuric acid. Then 129 g. (1 mole) of hydroxyethyl cyanoacetate was added dropwise with stirring while maintaining the reaction temperature below 75° C. The acylated ester thus produced was then diluted with 100 ml. of water and the excess acid was neutralized with solid potassium carbonate. The oil layer was separated and dried to yield 130 g. (79%) of the desired compound.

EXAMPLE 2

The method of Example 1 was repeated using an equivalent amount of propylene glycol and butanediol in place of ethylene glycol to provide the corresponding 3-acetoxypropyl cyanoacetate and 4-acetoxybutyl cyanoacetate intermediates, respectively, in high yield.

What we claim is:

1. Acetoxyalkyl cyanoacetate compounds having the formula:

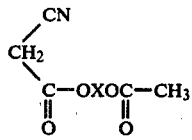

where X is alkylene, $C_2$–$C_{17}$, unsubstituted or substituted with halo, cyano, alkyl, $C_1$–$C_6$, alkoxy, $C_1$–$C_6$, alkoxyalkyl, $C_1$–$C_6$, or alkoxyalkyleneoxy, $C_1$–$C_6$.

2. A compound according to claim 1 whwerein X is unsubstituted $C_2$–$C_6$.

3. A compound according to claim 1 which is acetoxyethyl cyanoacetate.

4. A compound according to claim 1 which is 3-acetoxypropyl cyanoacetate.

5. A compound according to claim 1 which is 4-acetoxybutyl cyanoacetate.

* * * * *